United States Patent [19]

Skov et al.

[11] 4,183,953

[45] Jan. 15, 1980

[54] AQUEOUS AMMONIUM ISOBUTYRATE-ISOBUTYRIC ACID SOLUTION USEFUL FOR PRESERVING SEEDS, SILAGE, AND OTHER FEEDSTUFF

[75] Inventors: Ebbe R. Skov, Sao Paulo, Brazil; Roderick B. Judge, Montclair; Geoffrey Hemphill, Manasquan, both of N.J.

[73] Assignee: W. R. Grace & Co., New York, N.Y.

[21] Appl. No.: 889,010

[22] Filed: Mar. 22, 1978

Related U.S. Application Data

[63] Continuation-in-part of Ser. No. 709,118, Jul. 27, 1976, abandoned, which is a continuation of Ser. No. 557,890, May 15, 1975, abandoned, which is a continuation-in-part of Ser. No. 407,106, Oct. 17, 1973, Pat. No. 3,899,588, which is a continuation-in-part of Ser. No. 304,462, Nov. 7, 1972, Pat. No. 3,786,086.

[51] Int. Cl.$^2$ ............... A01N 9/02; A01N 9/24
[52] U.S. Cl. ................................... 424/317
[58] Field of Search ........................... 424/317

[56] References Cited

U.S. PATENT DOCUMENTS

| | | | |
|---|---|---|---|
| 2,154,449 | 4/1939 | Hoffman et al. | 426/9 |
| 3,123,632 | 3/1964 | Katzschmann | 260/475 |
| 3,488,386 | 1/1970 | Rice, Jr. | 260/541 |
| 3,579,297 | 5/1971 | Ekblom | 423/313 |
| 3,595,665 | 7/1971 | Huitson et al. | 424/317 |
| 3,806,600 | 4/1974 | Lapore et al. | 424/317 |
| 3,895,116 | 7/1975 | Herting et al. | 424/317 |

FOREIGN PATENT DOCUMENTS

| | | |
|---|---|---|
| 544335 | 7/1956 | Belgium . |
| 376628 | 9/1938 | Canada . |
| 2175629 | 10/1973 | France . |
| 51387 | 6/1966 | Poland . |
| 1255205 | 12/1971 | United Kingdom . |

OTHER PUBLICATIONS

Chemical Abstracts, vol. 59 (1963), p. 2098c.
Zuffanti, J.A.C.S., vol. 63 (1941), pp. 3123-3124.
Chemical Abstracts, vol. 68 (1968), p. 12487f.
Chemical Abstracts, vol. 62 (1965), pp. 15,490h-15,491a.

*Primary Examiner*—V. D. Turner
*Attorney, Agent, or Firm*—Elton Fisher; Edward J. Cabic

[57] ABSTRACT

An aqueous solution comprising ammonium isobutyrate and isobutyric acid is useful for preventing the development of rot and mildew on seeds, silage, and other feedstuff. Said solution has a crystallization temperature between about −20° F. and −40° F.

11 Claims, 9 Drawing Figures

FIG. 2
CRYSTALIZING TEMPERATURES OF AmnIB SOLUTIONS AS A FUNCTION OF FREE IBA CONTENT

FIG. 1
SOLUBILITY OF AMMONIUM ISOBUTYRATE IN WATER AS A FUNCTION OF TEMPERATURE

FIG. 4
VISCOSITY AS A FUNCTION OF TEMPERATURE

55% NOMINAL AmnIB
47.2% ACTUAL AmnIB
6.4% FREE IBA

FIG. 3
pH AS A FUNCTION OF FREE IBA CONTENT

▽ 65% NOMINAL AmnIB
□ 60% NOMINAL AmnIB
○ 55% NOMINAL AmnIB

FIG. 8
REFRACTIVE INDEX AS A FUNCTION OF pH

FIG. 7
SPECIFIC CONDUCTANCE AS A FUNCTION OF FREE IBA CONTENT

FIG. 9

AQUEOUS AMMONIUM ISOBUTYRATE-ISOBUTYRIC ACID SOLUTION USEFUL FOR PRESERVING SEEDS, SILAGE, AND OTHER FEEDSTUFF

CROSS-REFERENCES TO RELATED APPLICATIONS

This is a continuation-in-part of our application Ser. No. 709,118, filed July 27, 1976, and now abandoned. Said application Ser. No. 709,118 is a continuation of our application Ser. No. 577,890, filed May 15, 1975, and now abandoned. Said application Ser. No. 577,890 is a continuation-in-part of our application Ser. No. 407,106, filed Oct. 17, 1973, and now U.S. Pat. No. 3,899,588, which is, in turn a continuation-in-part of our application Ser. No. 304,462, filed Nov. 7, 1972, and now U.S. Pat. No. 3,786,086.

The benefit of each of said applications is claimed, and each, in its entirety, is incorporated herein by reference.

BACKGROUND OF THE INVENTION

This invention is in the field of ammonium isobutyrate (AmnIB). More specifically it is in the field of a solution comprising water, AmnIB, and isobutyric acid (IBA), said solution being useful for preventing rot and mildew from forming on seeds, silage, and other feedstuff.

U.S. Pat. No. 3,846,567 (Matyas, et al.) teaches the use of propionic acid to inhibit microbiological deterioration of feedstuff such as silage, fodder, or maize.

U.S. Pat. No. 3,806,600 (Lapore, et al.) teaches the use of salts of alkanoic acids, including AmnIB, to inhibit the growth of microorganisms in animal feedstuff.

U.S. Pat. No. 3,595,665 (Huitson, et al.) teaches the use of formic acid or binary and ternary mixtures of formic, acetic, and propionic acids to prevent mold growth on animal feedstuff.

U.S. Pat. No. 2,154,449 (Hoffman, et al.) teaches the use of certain salts including calcium propionate, sodium or potassium propionate, ammonium butyrate, and AmnIB for inhibiting the growth of mold in materials including foodstuffs which are susceptible thereto.

Canadian Pat. No. 376,628 (Hoffman, et al.) teaches a method for inhibiting mold growth on materials susceptible thereto, excepting baked goods, comprising treating the surface of such material with a saturated aliphatic monocarboxylic acid of from 3 to 12 carbon atoms.

SUMMARY OF THE INVENTION

In summary this invention is directed to a solution useful for preventing rot and mildew from forming on seeds and feedstuff, said solution: (a) consisting essentially of water, ammonium isobutyrate, and isobutyric acid; and (b) having: (i) a nominal ammonium isobutyrate content of about 54–62%; (ii) a viscosity of about 40–65 or 35–75 centiposes at about 10°–20° F.; (iii) a density of about 8.67–8.68 pounds per gallon at 78° F.; and (iv) an actual isobutyric acid content effective for causing: (A) the pH of the solution to fall within a range of about 6.8–7.2; and (B) the crystallization temperature (the salting out temperature) of the solution to fall within a range of about −20° F. to about −40° F.

BRIEF DESCRIPTION OF THE DRAWINGS

FIGS. 4, 5, and 6 are a series of curves showing the viscosity in centipoises of the system ammonium isobutyrate-isobutyric acid-water as a function of temperature.

DESCRIPTION OF OTHER EMBODIMENTS

In another embodiment ("Embodiment A") this invention is directed to a solution useful for preventing rot and mildew from forming on seeds and feedstuff, said solution: (a) consisting essentially of water, ammonium isobutyrate, and isobutyric acid; and (b) having: (i) a nominal ammonium isobutyrate content of about 54–62%; (ii) an actual isobutyric acid content of about 2–9% or 2.5–8.5% or 3–8%, or 4–8%, or 4–7%; (iii) a crystallization temperature of about −20° F. to about −40° F. (about −29° C. to about −40° C.); and (iv) a viscosity of about 10 to 30 centipoises at 50° F.

In another embodiment the solution of the above Summary has an actual isobutyric acid content within a range of about 2–9%, or 2.5–8.5, or 3–8%, or 4–8% or 4–7%.

In still other embodiments each solution of this invention has:
1. A coefficient of expansion of about −0.0024 to about −0.0027 pound per U.S. gallon per degree F over a temperature range of 32° F. to 78° F. (0° C. to 25.6° C.).
2. A specific conductance of about $3.1 \times 10^{-2}$ Mhos per centimeter to about $4 \times 10^{-2}$ Mhos per centimeter.
3. A nominal ammonium isobutyrate content of 55–60% and a specific conductance of about $3.3 \times 10^{-2}$ Mhos per centimeter to about $4 \times 10^{-2}$ Mhos per centimeter at 78° F.
4. A refractive index of about 1.406 to about 1.416 at 77° F. (25° C.) at a pH of about 6.8–7.2.
5. A viscosity of about 35–75 centipoises at about 10°–20° F.

In another embodiment the solution of Embodiment A has a density of about 8.67–8.68 pounds per U.S. gallon. The solution of Embodiment A also has a pH of about 6.8–7.2 and a refractive index of about 1.406 to about 1.416 at 77° F.

DETAILED DESCRIPTION OF THE INVENTION

Unlike aqueous solutions of ammonium isobutyrate (($CH_3)_2CHCOONH_4$) per se which are basic (e.g., a 60% aqueous ammonium isobutyrate solution has a pH of about 8.2), the solution of our invention is neutral or substantially neutral having a pH of 7.0±0.2.

It has been found that the composition of: (a) the above summary; and (b) the other above-mentioned embodiments is an excellent and effective composition for preventing the formation of rot and mildew on seeds, silage, and other feedstuff. This composition is especially effective for preventing rot caused by bacteria, or by mold, or by both bacteria and mold in stored silage.

Said composition can be prepared by admixing predetermined amounts of water, ammonium isobutyrate (AmnIB), and isobutyric acid (IBA) and agitating (e.g., stirring or shaking) the resulting mixture until the AmnIB (a solid salt) dissolves.

Figure 9:
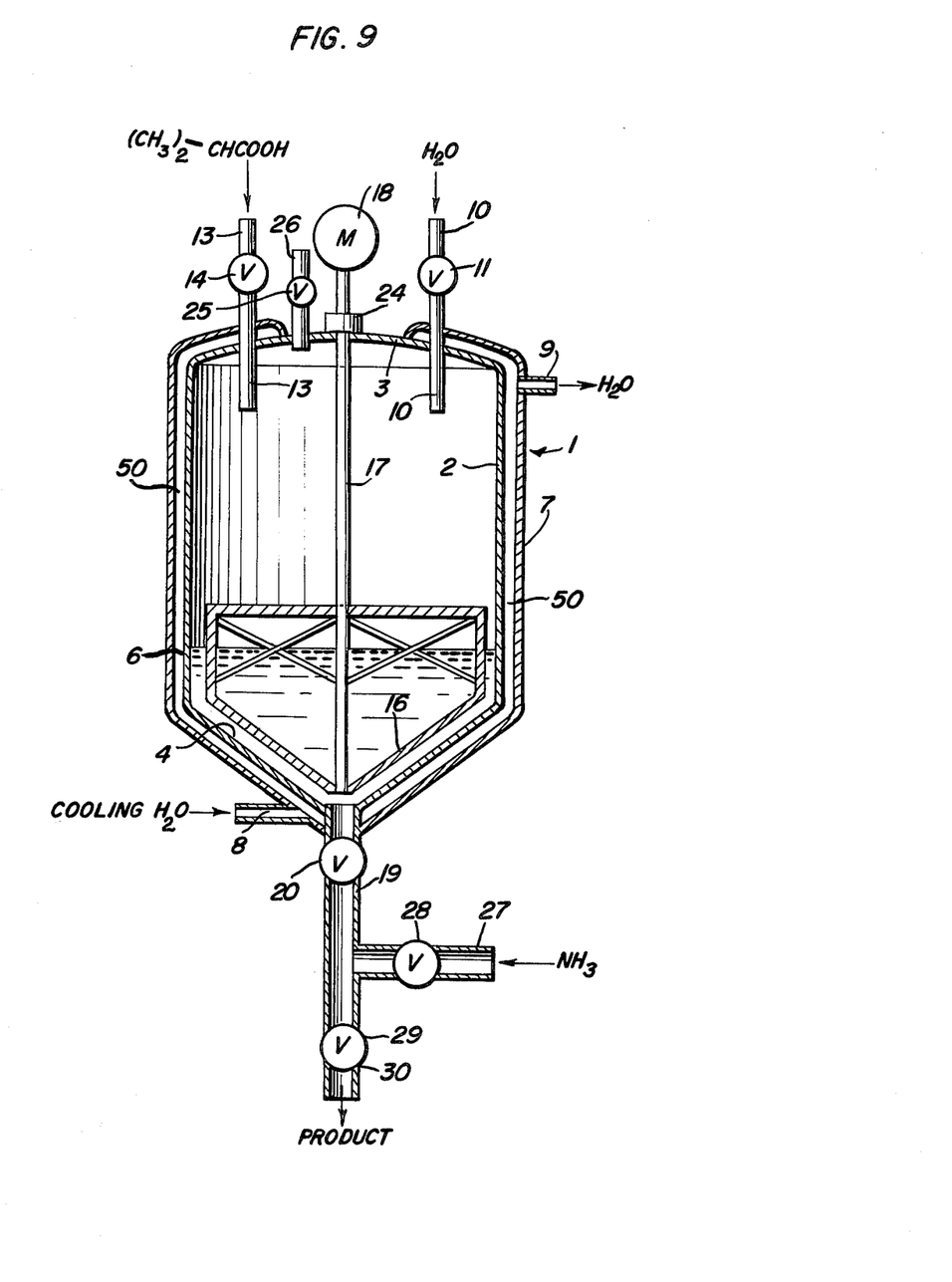
FIG. 9 shows, in section, with parts cut away, an apparatus useful for preparing the solution of this invention. Great grandparent application Ser. No. 407,106, filed Oct. 17, 1973 (now U.S. Pat. No. 3,899,588) presents details on the use of this apparatus.

Alternatively, the composition can be prepared by dissolving IBA in water and reacting a portion of the dissolved IBA with ammonia to form the composition of this invention. FIG. 9 of the drawings shows an apparatus which is useful for preparing our solution by this method.

Referring to FIG. 9: A predetermined amount of water is charged into the reactor shown generally at 1 via port 10 and valve 11 and a predetermined amount of IBA is charged into the reactor via port 13 and valve 14. Agitation means 16 which is driven by motor 18 via shaft 17 which enters the top 3 of reactor 1 through bushing 24 is used to admix the water and the IBA and subsequently to agitate this mixture while adding ammonia (preferably anhydrous liquid ammonia, but anhydrous ammonia vapor and aqueous ammonia are operable) thereto via line 27, valve 28, line 19 and valve 20. Cooling water is supplied as needed to cooling space 50 (which is between walls 6 and 7) via line 8. The cooling water leaves said jacket via line 9. Vent line 26 and valve 25 are used as a vent where charging or discharging reactor 1 Line 26 can be connected to a scrubber (not shown) when charging reactor 1. After the desired amount of ammonia has been added and the reaction is completed, the liquid solution (product) is discharged (removed) from reactor 1 via lines 19 and 30, and valves 20 and 29. Such apparatus and its use is described in U.S. Pat. No. 3,899,588.

The solutions of this invention can also be prepared in a tubular reactor which is a preferred method where operating on a commercial scale. U.S. patent application Ser. No. 745,840; (Funk, et al, inventors) filed Nov. 29, 1976 and now abandoned teaches the use of such reactor. Said patent application which is assigned to W. R. Grace & Co. is incorporated herein by reference.

It is well known to those skilled in the art that solid particulate AmnIB can be applied to seeds, silage, or other feedstuff to prevent or substantially prevent rot and mildew from forming thereon. However, because of the fact that particulate AmnIB cakes on standing—setting to form large hard lumps which are difficult to break into small pieces—it is exceedingly difficult to apply solid particulate AmnIB at an even rate to seeds or other feedstuff to prevent rot and mildew from growing thereon. Such caking may occur where the particulate AmnIB is packaged for a short time (e.g., 2–4 days or longer) even if packaged in substantially moisture proof drums or bags.

Accordingly, it is desirable to apply the AmnIB as a solution. However, where treating feedstuff—especially seeds such as corn, wheat, barley, oats, and the like—it is important that the amount of moisture added be kept low because an excessive moisture content favors the development of rot and mildew even in the presence of AmnIB (or other antirotting agents or antimildewing agents). Thus, where treating feedstuff it is important that the moisture (water) content of the AmnIB solution does not exceed about 40–45% (or about 39–46%).

Figure 1:
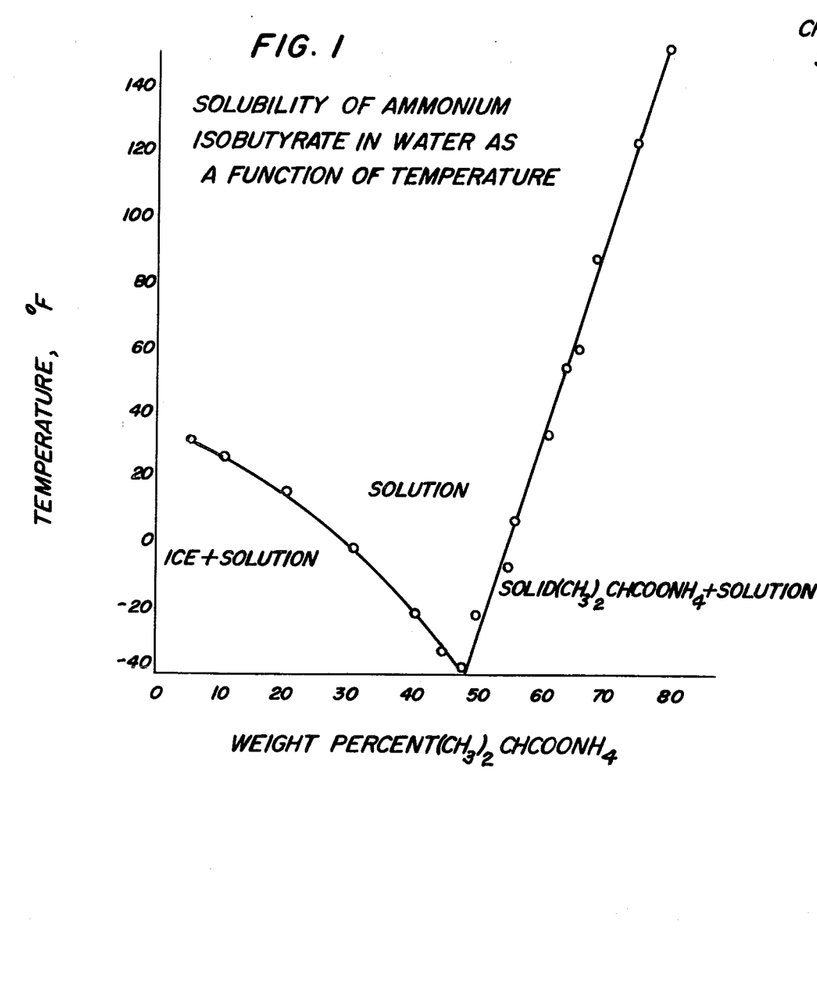
FIG. 1 is a phase diagram showing crystallization temperatures of the system ammonium isobutyrate-water, said system being free of isobutyric acid $((CH_3)_2CHCOOH)$ per se. Hence, a 10% ammonium isobutyrate solution of the type represented by FIG. 1 actually contains 10 parts by weight of $(CH_3)_2CHCOONH_4$ and 90 parts by weight of water while a 60% solution actually contains 60 parts by weight of $(CH_3)_2CHCOONH_4$ and 40 parts by weight of water.

Unfortunately, as shown by FIG. 1, an aqueous AmnIB solution containing 40% water crystalizes at about 32° F. (0° C.) thereby precluding the use of such aqueous AmnIB in many parts of the United States in late fall because drums or tanks of AmnIB solution would generally be stored on farms (or in many distribution centers) in unheated areas or, more likely, out of doors where the temperature of such solutions can drop well below 0° F. (ca. −18° C.) thereby causing a serious crystallization problem which could render the AmnIB solution nonpumpable and hence unusable.

It is true that, in so far as water content and crystallization temperatures are concerned, isobutyric acid (IBA) could be substituted for aqueous AmnIB solutions. However, such substitution would introduce substantially unmanageable difficulties caused by the corrosive nature of IBA. Thus, if IBA or an aqueous solution of IBA (e.g., 60% IBA) were used in place of AmnIB, it would be necessary for the operator to avoid contacting his person and clothing (except moisture proof rubber or plastic protective clothing) with the IBA solution. Further, mild steel pumps, storage tanks, storage drums, pipes, and the like could not be used because of serious corrosion. This would necessitate the use of stainless steel or other expensive apparatus.

We have found that the aqueous solution described in the above summary and preferred embodiments (said solution consisting essentially of water, AmnIB, and free IBA) can be used for treating seeds and feedstuff—including silage, hay, and the like—without introducing too much water into the treated feedstuff, and also without presenting the corrosivity problem of IBA or aqueous IBA solutions which contain about 40-60% or 55-60% IBA. On the contrary, the solution of our invention can be used without protective clothing (except for goggles to protect the operator's eyes). Further, the solution of our invention can be stored and transported in mild steel tanks or drums and mild steel pumps and pipes can be used to apply it (the solution of our invention) to feedstuff to be protected against rot and mildew. Further, the solution of our invention has a very low crystallization temperature (e.g., ca. $-20°$ to $-40°$ F.). Hence, crystallization where the solution of our invention is stored in unheated areas is not a serious problem in most sections of the northern United States at the time of year (autumn or late autumn) when major amounts of it are applied to feedstuff.

As noted supra, the solution of our invention can be prepared by:

1. Admixing water, ammonium isobutyrate, and isobutyric acid in predetermined amounts. Where using this procedure the amount of water added is decreased by an amount equal to that present in: (a) the ammonium isobutyrate; and (b) the isobutyric acid (both of which frequently contain some water), and the weight amount of ammonium isobutyrate and/or isobutyric acid used is adjusted because of such water so that the desired amounts of ammonium isobutyrate per se and isobutyric acid per se are actually provided.

2. Admixing water, isobutyric acid and ammonia (anhydrous ammonia or aqueous ammonia). Where using this procedure adjustments are also made to take into account the presence of water (if any) in the isobutyric acid and/or ammonia.

For convenience in preparing our solutions and in making the calculations necessary for preparing such solutions we use the following conventions:

"Actual Ammonium Isobutyrate" is the $(CH_3)_2CHCOONH_4$ present in a solution of our invention.

"Actual Isobutyric Acid" (or "Free Isobutyric Acid") is the $(CH_3)_2CHCOOH$ present in a solution of our invention.

"Nominal Ammonium Isobutyrate" is the actual ammonium isobutyrate present in a solution of our invention plus the amount of $(CH_3)_2CHCOONH_4$ that would result if the actual isobutyric acid present in said solution were converted to actual ammonium isobutyrate according to the following equation:

$$NH_3 + (CH_3)_2CHCOOH = (CH_3)_2CHCOONH_4.$$

Since the molecular weights of ammonium isobutyrate is 105 and that of isobutyric acid is 88, each 88 parts by weight of isobutyric acid is treated (where calculating nominal ammonium isobutyrate) as though it were 105 parts by weight of ammonium isobutyrate.

Thus, where D is the parts of nominal ammonium isobutyrate per 100 parts of solution, E is the parts of actual ammonium isobutyrate $((CH_3)_2CHCOONH_4)$ per 100 parts of solution, F is the parts of actual (free) isobutyric acid $((CH_3)_2CHCOOH)$ per 100 parts of solution, G is the parts of water per 100 parts of solution, it follows that:

$D + G = 100$ parts (i.e., $D + G = 100\%$) and (Nominal % Ammonium Isobutyrate) $= [E] + [(105/88) \times (F)]$.

It is noted that our calculations are based on our definition wherein nominal percent ammonium isobutyrate plus percent water total (or equal) 100 percent.

Because of our above-presented conventions and definitions, 100 parts of a solution having a nominal 60% ammonium isobutyrate content will contain 40 parts of water and 60 parts of nominal ammonium isobutyrate.

Likewise, 100 parts of a solution of our invention having a nominal 55% ammonium isobutyrate content will contain 45 parts of water and 55 parts of nominal ammonium isobutyrate.

It will be noted that the actual amount of isobutyric acid (actual or free (uncombined) $(CH_3)_2CHCOOH$) present in a predetermined quantity of a solution of our invention is ignored where calculating the amount of water required to arrive at 100 parts (100%) because—for the purpose of said calculation—the actual or free isobutyric acid has been multiplied by the factor 1.19 (i.e., 105/88) and the resulting number $(1.19) \times (F)$ has been added to E to arrive at D (where E, F, and D are as defined supra).

It will also be noted, since our solution always contains both ammonium isobutyrate $((CH_3)_2CHCOONH_4)$ and free isobutyric acid $((CH_3)_2CHCOOH)$, that D is always greater than E because, as noted supra, D is the sum of $(1.19) \times (F)$ plus E (where E, F, and D are as defined supra).

Because of our above conventions and definitions it will be readily apparent that:

% Free Isobutyric Acid $= [(100) \times F]/[D + G]$.

The instant invention will be better understood by referring to the following specific but nonlimiting examples. It is understood that said invention is not limited by these examples which are offered merely as illustrations; it is also understood that modifications can be made without departing from the spirit and scope of the invention.

The examples were actually run.

EXAMPLE 1

Solutions for use in obtaining the data represented by the points shown in FIG. 1 were prepared by dissolving predetermined amounts of substantially pure ammonium isobutyrate in predetermined amounts of water and thoroughly admixing the resulting solution.

The resulting solutions were analyzed for nitrogen by the Kjeldahl method before determining their crystallization temperatures.

EXAMPLE 2

The crystallization temperatures of the ammonium isobutyrate solutions prepared in Example 1 were determined by the following method:

Method No. 1

This method was used with solutions crystallizing below about 35° C.

In each instance a portion of the solution under study was placed in a jacketed tube provided with a stopper and fitted with an alcohol thermometer and an efficient stirring means.

The jacketed tube was placed in a cold bath, and the temperature, as indicated by the thermometer, was observed while the solution was being stirred. The temperature fell gradually until a solid phase appeared, and the first steady temperature after any intitial supercooling effect has disappeared was taken as the crystallization temperature.

This technique is described on pgs. 222-223 of Daniels and Alberty, "Phsical Chemistry", John Wiley & Sons, Inc., New York, N.Y., 1955.

Method No. 2

Crystallization temperatures of ammonium isobutyrate solutions crystallizing above about 35° C. were determined using a variable temperature shaker-water bath Model 2156, manufactured by Research Specialities Company, Richmond, California. Stoppered Erlenmeyer flasks (250 ml) each containing 100 ml of test solution were cycled between narrow extremes of temperature above and below the crystallizing (salting-out) temperatures of the respective liquids. The crystallizing temperature was interpreted as the point where crystals could first be seen as the temperature was lowered at intervals of 1° F. (ca 0.5° C.).

EXAMPLE 3

Ammonium isobutyrate solutions which contain free (uncombined) isobutyric acid used to obtain the data represented by: (a) the points shown in FIGS. 2-8; and (b) the values reported in Table 1 were prepared by admixing predetermined amounts of water, substantially pure ammonium isobutyrate, and substantially pure isobutyric acid.

In each instance the resulting solution was analyzed for actual ammonium isobutyrate by the Kjeldahl (nitrogen determination) method and for total isobutyrate radical by titration with standard base in the presence of sufficient formaldehyde to complex the ammonium nitrogen of the ammonium isobutyrate.

EXAMPLE 4

Figure 2:
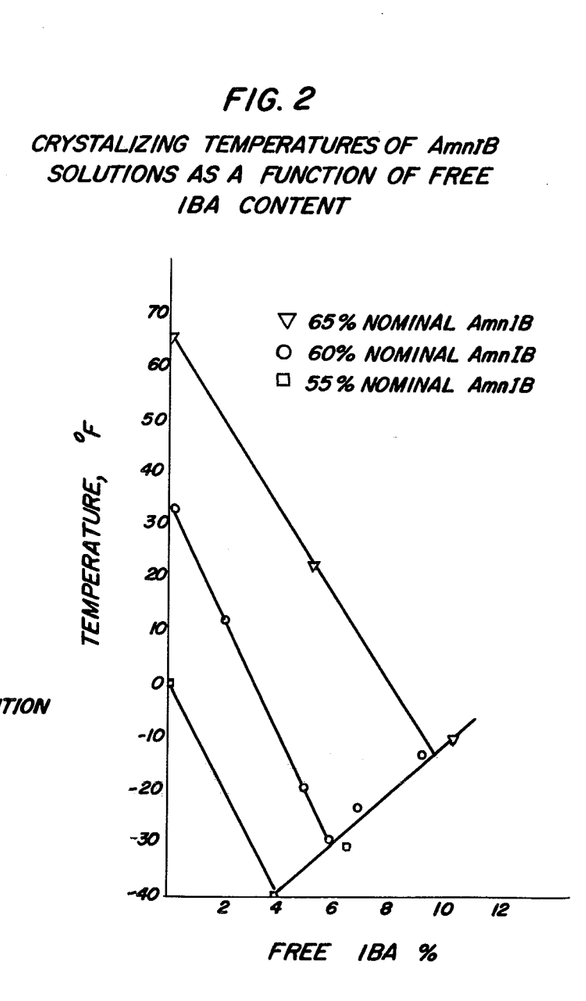
FIG. 2 is a phase diagram showing crystallization temperatures of the system ammonium isobutyrate-isobutyric acid-water where said system has a nominal ammonium isobutyrate content (as defined infra) of: (a) 55%; (b) 60%; and (c) 65% with the actual (free) isobutyric acid content (as defined infra) thereof varying from 0% to about 11%.

The crystallization data shown in FIG. 2 were obtained by Method No. 1 of Example 2.

EXAMPLE 5 pH values were, in each instance determined with a glass electrode type pH meter.

Figure 3:
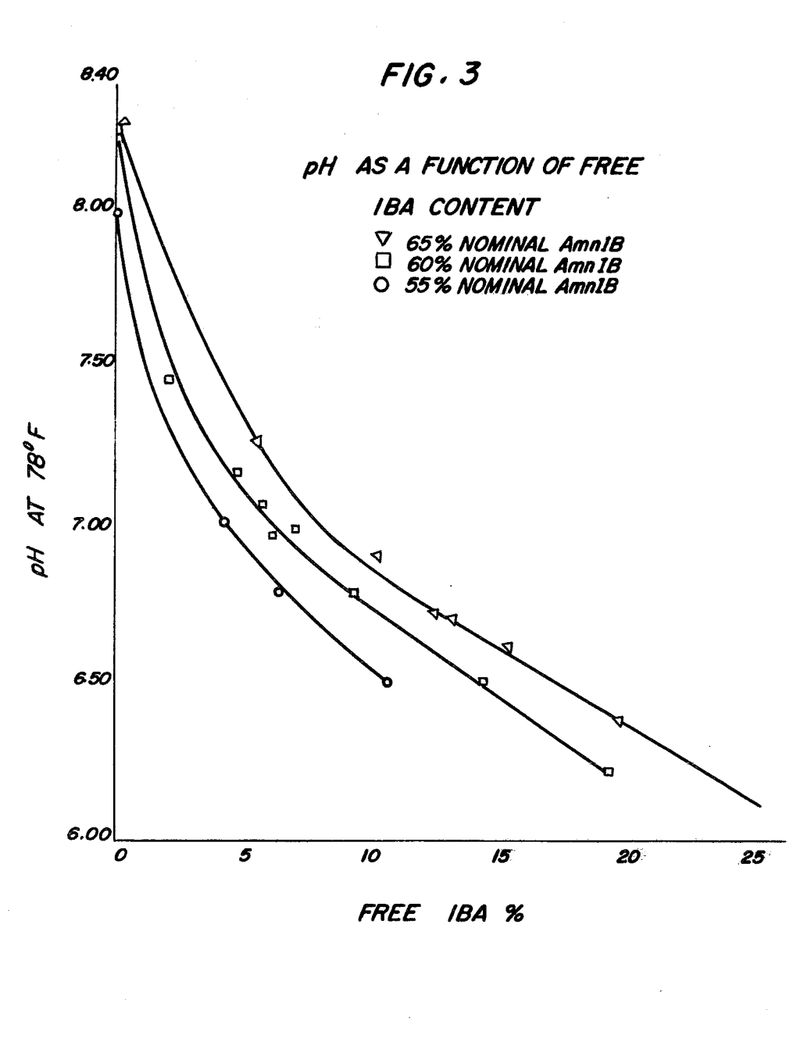
FIG. 3 is a series of curves showing the effect of actual isobutyric (free) acid content on the pH of the system ammonium isobutyrate-isobutyric acid-water (where said system has a nominal ammonium isobutyric acid content of 55%, 60% and 65%) over the range of 0 to about 10% actual isobutyric acid.

See FIG. 3 for pH data.

EXAMPLE 6

Figure 4:
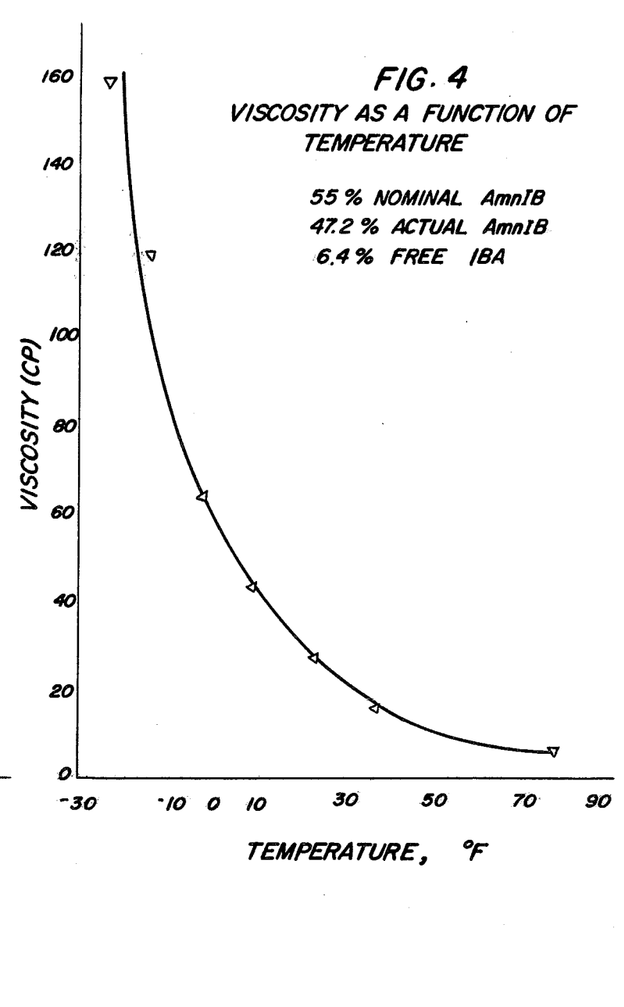
FIG. 4 shows the viscosity of such system having a nominal ammonium isobutyrate content of 55%, an actual ammonium isobutyrate content of 47.2%, and a free (actual) isobutyric acid content of 6.4%.
Figure 5:
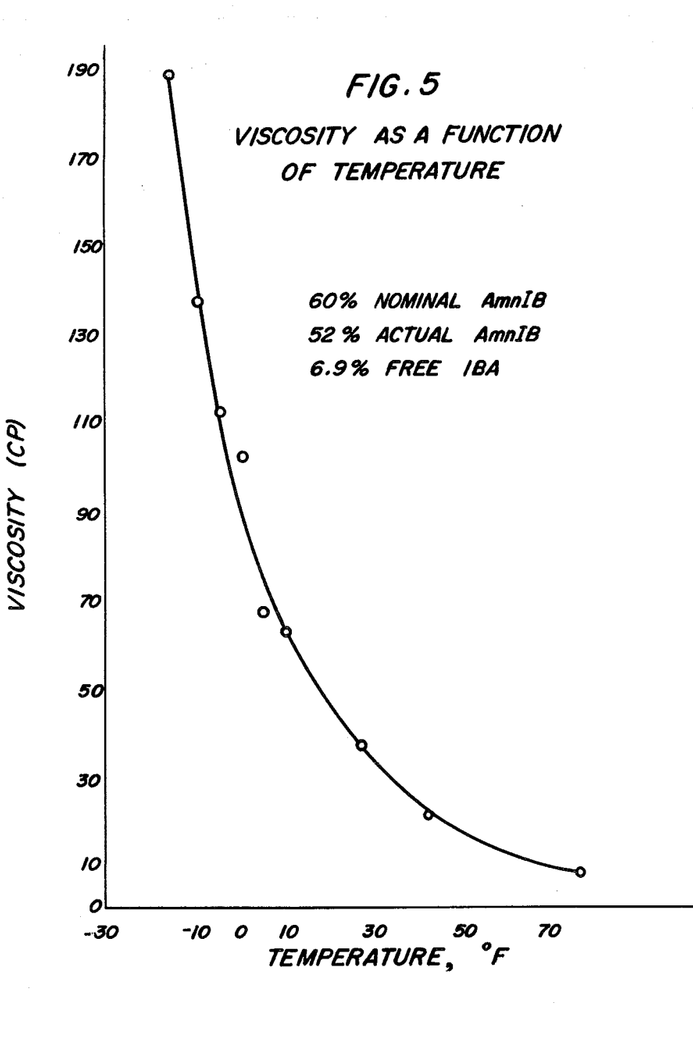
FIG. 5 shows the viscosity of such system having a nominal ammonium isobutyrate content of 60%, an actual ammonium isobutyrate content of 52%, and a free isobutyric acid content of 6.9%.
Figure 6:
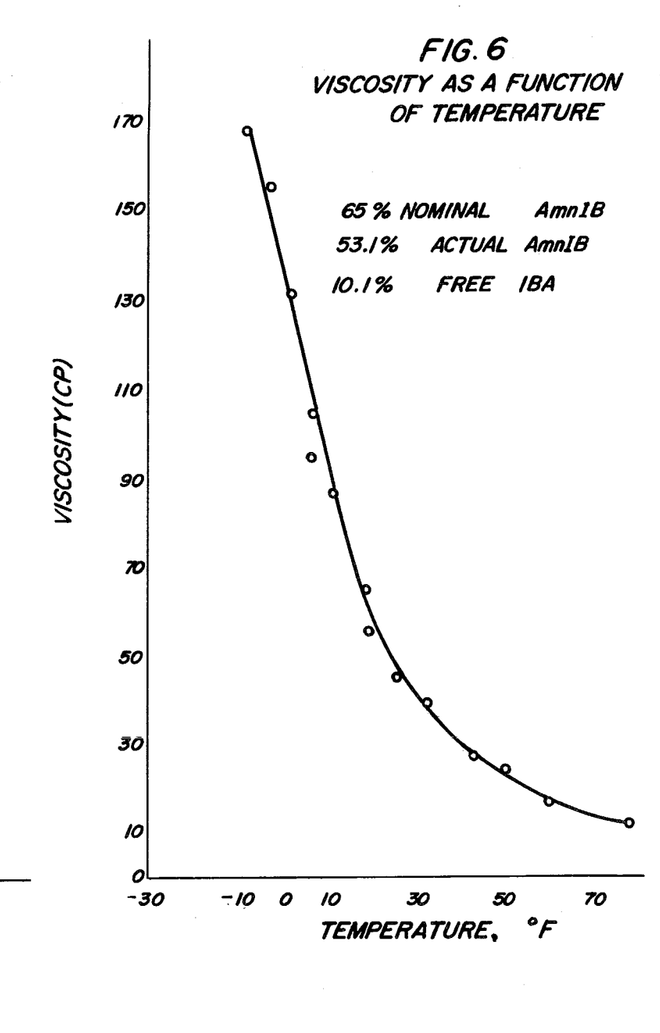
FIG. 6 shows the viscosity of such system having a nominal ammonium isobutyrate content of 65%, an actual ammonium isobutyrate content of 53.1%, and a free isobutyric acid content of 10.1%.

The viscosity data reported in FIGS. 4-6 were determined with a Model LVT Brookfield Viscometer. Readings were made at 60 revolutions per minute using: (a) a No. 1 spindle at temperatures greater than 32° F.; and (b) a No. 2 spindle at temperatures less than 32° F.

It was observed that at temperatures above the temperature required for crystal formation the solutions behaved as Newtonian fluids (i.e., the viscosity remained essentially constant regardless of the rate of shear.) At temperatures below where ice or crystal growth occured, the systems behaved as non-Newtonian fluids.

TABLE 1
VARIATION OF DENSITY AND COEFFICIENT OF EXPANSION WITH TEMPERATURE

| Solution Composition | | Density | | | | Coefficient of Expansion |
|---|---|---|---|---|---|---|
| Nominal % AmnIB* | Actual % IBA** | 78° F. | | 32° F. | | (lb/gal/°F.) |
| | | g/ml | lb/gal | g/ml | lb/gal | 32° to 78° F. |
| 55.0 | 0.0 | 1.041 | 8.683 | 1.057 | 8.818 | −0.0029 |
| | 4.1 | 1.038 | 8.661 | 1.051 | 8.773 | −0.0024 |
| | 6.4 | 1.037 | 8.654 | 1.052 | 8.778 | −0.0027 |
| | 10.5 | 1.033 | 8.619 | 1.048 | 8.741 | −0.0027 |
| 60.0 | 0.0 | 1.040 | 8.674 | 1.054 | 8.796 | −0.0027 |
| | 2.0 | 1.039 | 8.673 | 1.054 | 8.797 | −0.0027 |
| | 6.9 | 1.037 | 8.654 | 1.051 | 8.771 | −0.0025 |
| | 14.2 | 1.031 | 8.600 | 1.047 | 8.738 | −0.0030 |
| 65.0 | 0.0 | 1.038 | 8.661 | — | — | — |
| | 5.3 | 1.036 | 8.646 | 1.053 | 8.787 | −0.0031 |
| | 10.1 | 1.033 | 8.621 | 1.047 | 8.739 | −0.0026 |
| | 19.5 | 1.028 | 8.575 | 1.042 | 8.697 | −0.0027 |

*AmnIB means ammonium isobutyrate.
**IBA means isobutyric acid.

EXAMPLE 7

Figure 7:
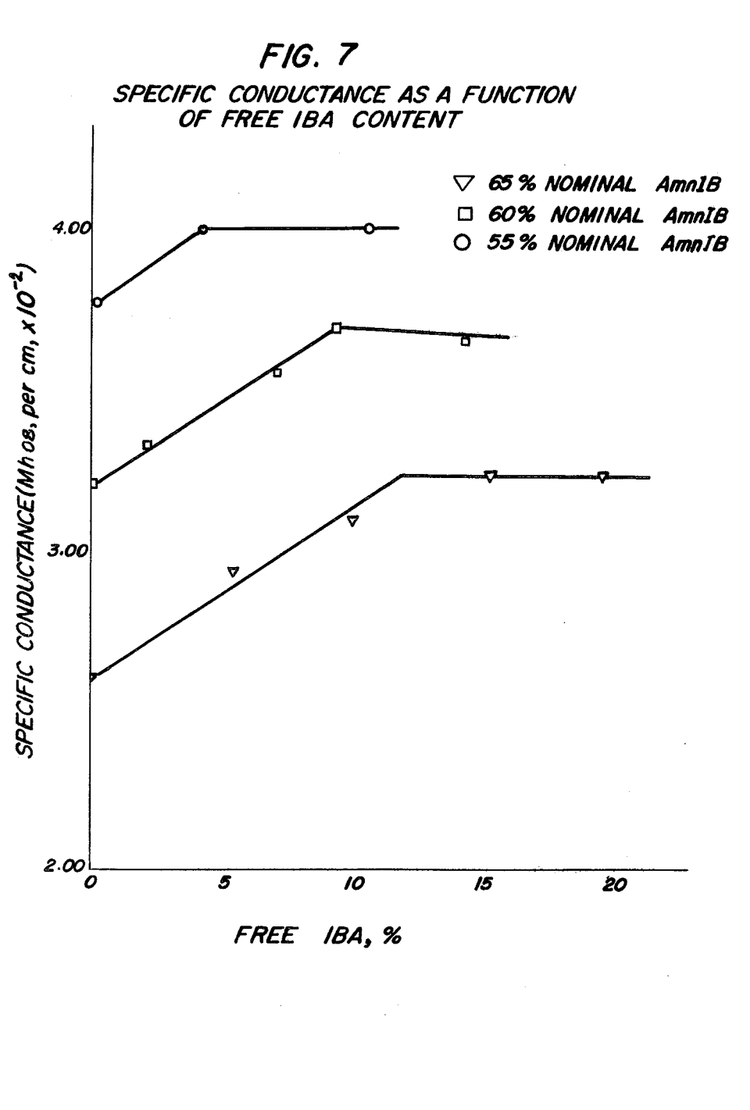
FIG. 7 is a series of curves showing the specific conductance at 78° F. of the system ammonium isobutyrate-isobutyric acid-water as a function of actual isobutyric acid content over the range of about 0–10% actual isobutyric acid where the system has a nominal ammonium isobutyrate content of 55%, 60%, and 65%.

The specific conductance data reported in FIG. 7 were determined with a Model RC-16B Conductivity Bridge manufactured by Industrial Instruments Inc., Jersey City, N.J. A test cell acting as one arm of a Wheatstone Bridge was immersed in the solution to determine resistance across the cell. Specific conductance in Mhos per cm was calculated by taking the reciprocal of the cell constant (k) times the resistance in ohms.

EXAMPLE 8

Figure 8:
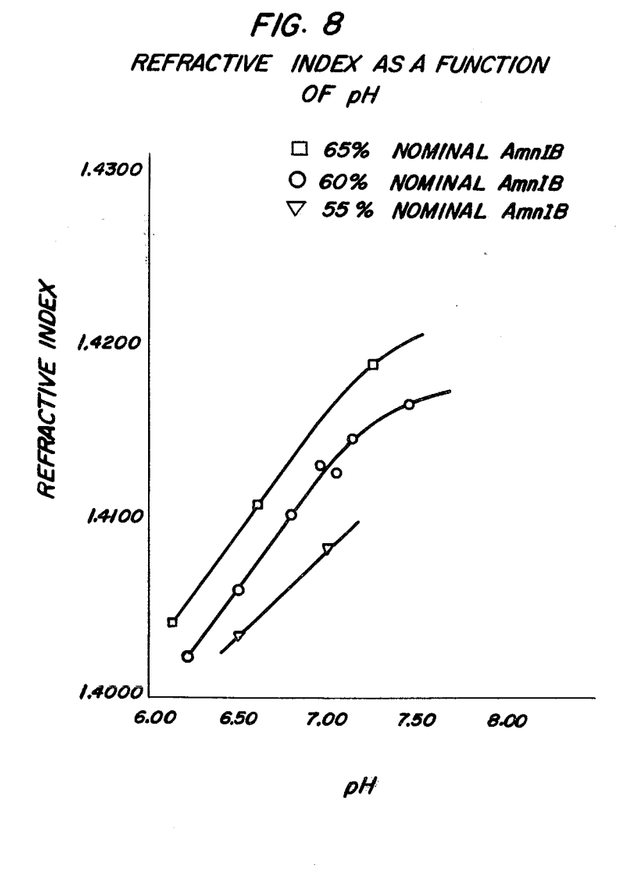
FIG. 8 is a series of curves showing refractive index of the system ammonium isobutyrate-isobutyric acid-water (where said system has a nominal ammonium isobutyrate content of 55%, 60%, and 65%) as a function of pH at 77° F. over the pH range of about 6.3–7.5.

The refractive index data reported in FIG. 8 were determined with a Bausch and Lomb refractometer. These measurements were made at 77° F. (25° C.).

EXAMPLE 9

The density data reported in Table 1 were determined by weighing known volumes of solution previously equilibrated at predetermined temperatures. Solutions were equilibrated for twenty-four hours at predetermined temperatures in tared 50 ml. volumetric flasks, adjusted to the mark and allowed to equilibrate to ambient conditions (room temperature) before reweighing.

These data were used to calculate the coefficients of expansion which are also reported in Table 1.

EXAMPLE 10

Dried cracked corn was admixed with water containing the level of additive ($(CH_3)_2CHCOONH_4$, or $(CH_3)_2CHCOOH$, or "Solution 7-A" (a solution of our invention consisting of ammonium isobutyrate, isobutyric acid, and water, said Solution 7-A having a nominal 60% ammonium isobutyrate content and a 5% actual isobutyric acid content) needed to form reconstituted cracked corn having a predetermined moisture content and a predetermined additive content. See Table 2 for details.

Solution 7-A was prepared by admixing substantially pure ammonium isobutyrate, substantially pure isobutyric acid and water.

Corn of 15% moisture content (70 g) was placed in a minature silo (4 oz glass jars). Water (30 g) containing the additive of weight given in Table 2, below, was added in each instance and the jar (silo) was capped, rolled for two hours on a roller and maintained at room temperature (20°-27° C.) until mold developed or for 40 days if no mold developed.

The results reported in Table 3 show that at application levels of 0.225% Solution 7-A is as effective as isobutyric acid at the same application level and at application levels of 0.45% and Solution 7-A is superior to ammonium isobutyrate at the same application level.

As used herein, the term "parts" means parts by weight unless otherwise defined where used.

As used herein, the term "percent (%)" means percent by weight unless otherwise defined where used.

As used herein, the term "actual isobutyric acid" (or its equivalent "free isobutyric acid") means isobutyric acid per se—i.e., $(CH_3)_2CHCOOH$.

As used herein, the term "actual ammonium isobutyrate" means ammonium isobutyrate per se—i.e., $(CH_3)_2CHCOONH_4$.

As used herein, the term "IBA" means isobutyric acid.

As used herein, the term "AmnIB" means ammonium isobutyrate.

TABLE 2

| Additive | Additive Content (Active Ingredients Added, %) | | | | | | |
|---|---|---|---|---|---|---|---|
| | .15 | .225 | .3 | .375 | .45 | .525 | .6 |
| Ammonium Isobutyrate Solution | .15 g | .225 g | .3 g | .375 g | .45 g | .525 g | .6 g |
| 7-A | .25 g | .375 g | .5 g | .625 g | .75 g | .875 g | 1.0 g |
| Isobutyric Acid | .15 g | .225 g | .3 g | .375 g | .45 g | .525 g | .6 g |

*Note that in each set of comparable runs the level of "active ingredient" is the same. The weight amounts of Solution 7-A are higher in each case because of the inert material (water) contained therein.

The length of time (in days) to molding, shown in Table 3 below, was judged from the point at which the cracked corn in the silo was evenly covered with mold, not from the first appearance of mold.

TABLE 3

| Additive | Days to Molding | | | | | | |
|---|---|---|---|---|---|---|---|
| | Additive Content (Active Ingredient Added, %) | | | | | | |
| | .15 | .225 | .3 | .375 | .45 | .525 | .6 |
| Ammonium Isobutyrate Solution | 3 | 3 | 4 | 4 | 15 | 18 | * |
| 7-A | 3 | 7 | 8 | 15 | * | * | * |
| Isobutyric Acid | 3 | 7 | 7 | 15 | 25 | * | * |
| Control (H₂O) | 3 | | | | | | |

*This run was terminated at the end of 40 days. No evidence of mold formation was observed up to the time the run was terminated.

We claim:

1. A solution useful for preventing rot and mildew from forming on feedstuff including seeds, said solution: (a) consisting essentially of water, ammonium isobutyrate, and isobutyric acid; and (b) having: (i) a nominal ammonium isobutyrate content of about 54–62%; (ii) an actual isobutyric acid content of about 2.5–8%; (iii) a crystallization temperature of about −20° F. to about −40° F.; and (iv) a pH of about 6.8–7.2.

2. The solution of claim 1 in which said solution has a density of about 8.67–8.68 pounds per gallon at 78° F.

3. The solution of claim 1 in which said solution has a nominal ammonium isobutyrate content of 55–60%.

4. The solution of claim 3 in which said solution has a density of about 8.67–8.68 pounds per gallon at 78° F.

5. The solution of claim 3 in which said solution has a coefficient of expansion of about −0.0024 to −0.0027 pound per gallon per degree F over a temperature range of 32° F. to 78° F.

6. The solution of claim 5 in which said solution has a refractive index of about 1.406 to about 1.416 at 77° F.

7. The solution of claim 3 in which said solution has a specific conductance of about $3.3 \times 10^{-2}$ Mhos per centimeter to about $4 \times 10^{-2}$ Mhos per centimeter.

8. The solution of claim 1 in which said solution has a coefficient of expansion of about −0.0024 to about −0.0027 pound per gallon per degree F over a temperature range of 32° F. to 78° F.

9. The solution of claim 8 in which said solution has a refractive index of about 1.405 to about 1.417 at 77° F.

10. The solution of claim 1 in which said solution has a specific conductance of about $3.1 \times 10^{-2}$ Mhos per centimeter to about $4 \times 10^{-2}$ Mhos per centimeter.

11. The solution of claim 1 in which said solution has a viscosity of about 35–75 centipoises at about 10°–20° F.

* * * * *